United States Patent [19]

Kanngiesser

[11] Patent Number: 5,416,581
[45] Date of Patent: May 16, 1995

[54] DEVICE AND PROCESS FOR MEASURING SOLID CONCENTRATIONS IN LIQUIDS

[75] Inventor: Hartmut Kanngiesser, Zurich, Switzerland

[73] Assignee: Zullig AG, Rheineck, Switzerland

[21] Appl. No.: 190,072

[22] PCT Filed: Jun. 1, 1993

[86] PCT No.: PCT/CH93/00141
§ 371 Date: Feb. 1, 1994
§ 102(e) Date: Feb. 1, 1994

[87] PCT Pub. No.: WO93/24824
PCT Pub. Date: Dec. 9, 1993

[30] Foreign Application Priority Data
Jun. 2, 1992 [CH] Switzerland ............... 1767/92

[51] Int. Cl.$^6$ .................. G01N 21/51; G01N 21/53
[52] U.S. Cl. ........................ 356/343; 356/442
[58] Field of Search ........... 356/336, 338, 339, 340, 356/343, 441, 442

[56] References Cited
U.S. PATENT DOCUMENTS

| | | | |
|---|---|---|---|
| 3,146,293 | 8/1964 | Lesage | 356/435 |
| 3,506,360 | 4/1970 | Albert | 356/339 |
| 3,553,462 | 1/1971 | Johnson | 356/343 |
| 4,914,310 | 4/1990 | Jarofski | |
| 5,012,119 | 8/1991 | Rhiner | |

FOREIGN PATENT DOCUMENTS

| | | |
|---|---|---|
| 3609156 | 9/1987 | Germany . |
| 3905101 | 9/1989 | Germany . |
| 57-119240 | 7/1982 | Japan . |
| 63-061144 | 3/1988 | Japan . |
| 1366922 | 1/1988 | U.S.S.R. ............ 356/343 |

OTHER PUBLICATIONS

Patent Abstracts of Japan, vol. 12, No. 280 (P-739)(3127) Aug. 1988.
Patent Abstracts of Japan, vol. 6, No. 212 (P-151)(1090) Oct. 1982.

Primary Examiner—Richard A. Rosenberger
Attorney, Agent, or Firm—Burns, Doane, Swecker & Mathis

[57] ABSTRACT

In a method for measuring solid concentrations in liquids, the light from two differently modulated sources (Q1, Q2) directed on the liquid is measured at the same time and processed in a combined multi-beam measuring process consisting of a 90° light scatter (Q1, P, D4; Q2, P, D3) and back-scatter process (Q1, P1, D1; Q2, P3, D2) and the solid concentration is found therefrom. The process is suitable for the simultaneous measurement of both extremely low and extremely high solid concentrations by using a 90° light scatter process for low concentrations and a back scatter process for high concentrations. The multi-beam process which is based on two measurements through exactly the same window areas makes it possible effectively to compensate for undesired soiling of the window areas. Mechanical devices for cleaning the window areas and to eliminate interfering light scatter are proposed.

17 Claims, 5 Drawing Sheets

DEVICE AND PROCESS FOR MEASURING SOLID CONCENTRATIONS IN LIQUIDS

The present invention relates to a device and a process for measuring solid concentrations in liquids, wherein the light from two sources directed at the liquid is simultaneously measured in a combined 90° scattered-light and backscatter process and processed, and from this the solid concentration is determined.

BACKGROUND AND SUMMARY OF THE INVENTION

In German Patent 3905101, a process and a device are described for measuring concentrations of suspended particles, the process being particularly suited for high particle concentrations. In this process light introduced into the suspension is scattered at the particles and measured at two locations at different distances. The particle concentration is determined from a combination of these measured values. This is done on the assumption that the introduced light is coupled into and out of the same window, which compensates for an eventual soiling of the window. The disadvantage of this is the fact that this assumption is only correct in specific situations, and that inaccurate measurements occur because of the window with nonhomogeneous soiling.

Processes for measuring low and minimal particle concentrations are known in water technology, where turbidity measurement is employed to assess the quality of drinking water, for example. Scattered-light processes are predominantly used for this. At low concentrations the term turbidity is generally used, whereas with high particle concentrations the terms predominantly used are solid content or solid concentrations. The term solid concentration (in g/l) will be used exclusively below, even with extremely low solid concentrations, where otherwise the term used would be turbidity values.

The object of the present invention is to disclose devices and processes with which solid concentrations, particularly low as well as high, can be determined with the same measuring process or the same measuring array via the 90° scattered light and backscatter.

In accordance with the invention, this object is attained by means of devices and processes in accordance with the wording in claims 1 through 12. Shown are:

The invention is described below in detail in conjunction with FIGS. 1 through 11.

DETAILED DESCRIPTION

Figure 1:
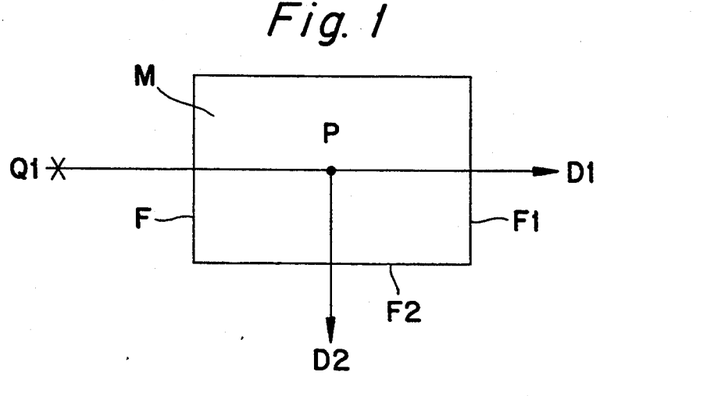
FIG. 1 a schematic representation of a 90° scattered-light process.

FIG. 1 shows a schematic representation of a known arrangement for a 90° scattered-light process.

Source Q1 transmits light through the window F onto the substance M to be measured, which contains particles P and is then encompassed by windows F1 and F2. The light from source Q1 is attenuated on the one hand by the substance M to be measured, and exits the substance through the window F1, after which it falls onto the detector D1, which corresponds to a transmission measurement in accordance with formula (1.1):

$$I_1/I_{D11} = exp(c\epsilon d)/(A_F A_{F1}) \qquad (1.1)$$

where
$I_i$ = light intensity of source i
$I_{Dji}$ = light intensity of source i at detector j
c = solid concentration
$\alpha_\gamma$ = scatter coefficient at angle $\gamma$
$\epsilon$ = absorption coefficient
$A_{Fi}$ = absorption factor in window $F_i$
d = light path in substance to be measured
$d_i$ = $i^{th}$ light path in substance to be measured The light of source Q1 is scattered on the other hand at particle P, whereupon it exits the substance to be measured at an angle of 90° through window F2 and falls onto detector D2, which corresponds to a scattered light measurement in accordance with formula (1.2):

$$I_1/I_{D21} = exp(c\epsilon d)/(\alpha_\pi c\, A_F A_{F2}) \qquad (1.2)$$

Formulas (1.1) and (1.2) are applicable, ignoring multiple scatterings in the substance to be measured.

Figure 2:
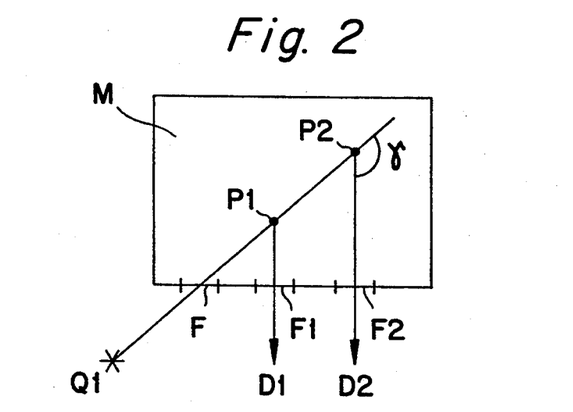
FIG. 2 a schematic representation of a backscatter process having two detectors and two different light paths.

FIG. 2 schematically shows a known arrangement for a backscatter process having two detectors.

Source Q1 transmits light through the window F onto the substance M to be measured, which contains particles P1 and P2 and is encompassed by windows F, F1 and F2. The light is scattered at particles P1 and P2, and the corresponding scattered light exits the substance to be measured at an angle $\gamma$ of 120°, for example, through windows F1 and F2, and falls upon the corresponding detectors D1 and D2, which corresponds to scattered light measurements in accordance with formulas (2.1) and (2.2):

$$I_1/I_{D11} = exp(c\epsilon d_1)/(\alpha_{120}\, c\, A_{F1}) \qquad (2.1)$$

$$I_1/I_{D21} = exp(c\epsilon d_2)/(\alpha_{120}\, c\, A_F A_{F2}) \qquad (2.2)$$

Formulas (2.1) and (2.2) are applicable, ignoring multiple scatterings in the substance to be measured.

Figure 3:
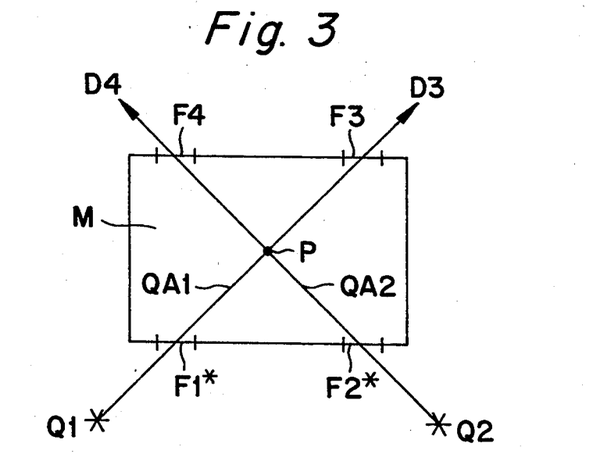
FIG. 3 a schematic representation of a multiple-beam process for 90° scattered light measurement having two sources and two detectors.

FIG. 3 shows a schematic representation of a multiple-beam measurement process for a 90° scattered light measurement having two sources and two detectors.

In this case sources Q1 and Q2 transmit differently modulated light. This light is detected with detectors D3 and D4, after interaction with particles P contained in the substance M to be measured. Source axes QA1 and QA2 of sources Q1 and Q2 are perpendicular to one another. The substance to be measured is encompassed by windows F1°, F2°, F3 and F4. Detectors D3 and D4 serve both to detect the transmitted light of the respective source located opposite and to detect the 90° scattered light of the source disposed perpendicular thereto. Ignoring multiple scatterings, formulas (3.1) and (3.2) apply for transmitted light measurement, and formulas (3.3) and (3.4) apply for the scattered light measurement:

$$I_1/I_{D31} = exp(c\epsilon d)/(A_{F1} \cdot A_{F3}) \tag{3.1}$$

$$I_2/I_{D42} = exp(c\epsilon d)/(A_{F2} \cdot A_{F4}) \tag{3.2}$$

$$I_1/I_{D41} = exp(c\epsilon d)/(\alpha_{90} \, c \, A_{F1} \cdot A_{F4}) \tag{3.3}$$

$$I_2/I_{D32} = exp(c\epsilon d)/(\alpha_{90} \, c \, A_{F2} \cdot A_{F3}) \tag{3.4}$$

Sources Q1 and Q2 and detectors D1 and D2 are disposed such that the corresponding light paths d are each of identical size.

In this way four measured values are obtained, from which the following relationships are formed:

$$I_{D41}/I_{D31} = \alpha_{90} \, A_{F4}/A_{F3} \tag{3.5}$$

$$I_{D32}/I_{D42} = \alpha_{90} \, c \, A_{F3}/A_{F4} \tag{3.6}$$

Formulas (3.5) and (3.6) are independent of source intensities $I_1$ and $I_2$ and of the damping $exp(c\epsilon d)$ in the substance to be measured.

If sources Q1 and Q2 are controlled such that condition (3.7) is met, then multiplication of formula (3.5) with (3.6) yields the result (3.8):

$$I_{D31} = I_{D42} = k \tag{3.7}$$

$$I_{D32} \, I_{D41} = (\alpha_{90} \, c)^2 \, k^2 \tag{3.8}$$

where the measured light intensities $I_{D32}$ and $I_{D41}$ are now dependent only on the scatter coefficient $\alpha_{90}$, a constant k and the solid concentration c.

Figure 4:
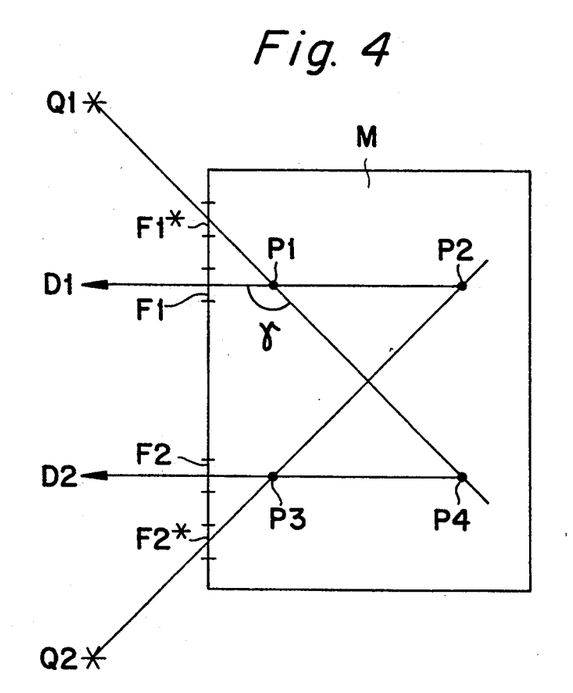
FIG. 4 a schematic representation of a multiple-beam process in accordance with the invention for backscatter measurement having two sources and two detectors.

FIG. 4 shows a schematic representation of a multiple-beam process of the invention for a backscatter measurement having two sources and two detectors.

In this instance sources Q1 and Q2 transmit differently modulated light, which is coupled into the substance M to be measured through windows F1° and F2°. After interaction with particles P1, P2, P3 and P4 contained in the substance M to be measured, the light is detected with detectors D1 and D2. The substance to be measured is encompassed by windows F1, F1°, F2 and F2°, which are located in the same window surface, although this is not absolutely necessary. Detectors D1 and D2 serve to detect the backscatter at an angle γ of 135°. The following light paths result from this: $d_1$ from F1°-P1-F1, $d_2$ from F2°-P2-F1, $d_3$ from F2°-P3-F2 and $d_4$ from F1°-P4-F2. In particular, light paths $d_1$ and $d_3$, and $d_2$ and $d_4$, respectively, can be of equal size. The following formulas include this presupposition. Ignoring multiple scatterings, formulas (4.1) and (4.2) apply for backscatter measurement for source Q1, and formulas (4.3) and (4.4) apply for source Q2:

$$I_1/I_{D11} = exp(c\epsilon d_1)/(\alpha_{135} \, A_{F1} \cdot A_{F1}) \tag{4.1}$$

$$I_1/I_{D21} = exp(c\epsilon d_2)/(\alpha_{135} \, A_{F1} \cdot A_{F2}) \tag{4.2}$$

$$I_2/I_{D22} = exp(c\epsilon d_1)/(\alpha_{135} \, c \, A_{F2} \cdot A_{F2}) \tag{4.3}$$

$$I_2/I_{D12} = exp(c\epsilon d_2)/(\alpha_{135} \, c \, A_{F2} \cdot A_{F1}) \tag{4.4}$$

In this way 4 measured values are obtained, from which the following relationships (4.5) and (4.6) are formed:

$$I_{D11}/I_{D21} = exp[c\epsilon(d_2-d_1)]A_{F1}/A_{F2} \tag{4.5}$$

$$I_{D22}/I_{D12} = exp[c\epsilon(d_2-d_1)]A_{F2}/A_{F1} \tag{4.6}$$

Formulas (4.5) and (4.6) are independent of source intensities $I_1$ and $I_2$ and of the scatter coefficient $\alpha_{135}$ in the substance to be measured.

If sources Q1 and Q2 are controlled such that the condition (4.7) is met, then the result (4.8) is obtained through the multiplication of formula (4.5) with (4.6):

$$I_{D21} = I_{D12} = k \tag{4.7}$$

$$I_{D11} \, I_{D22} = k^2 \, exp[2c\epsilon(d_2-d_1)] \tag{4.8}$$

where the measured light intensities $I_{D11}$ and $I_{D22}$ are now dependent only on the difference between the light paths $d_1$ and $d_2$, which are constant; on the absorption coefficient $\epsilon$; on a constant k; and on the solid concentration c.

By means of a skillful spatial arrangement, the two measuring processes in FIG. 3 and FIG. 4 can be combined so that the same sources Q1 and Q2 can be used. The electronics required for evaluation are practically identical in the two measuring processes.

Figure 5:
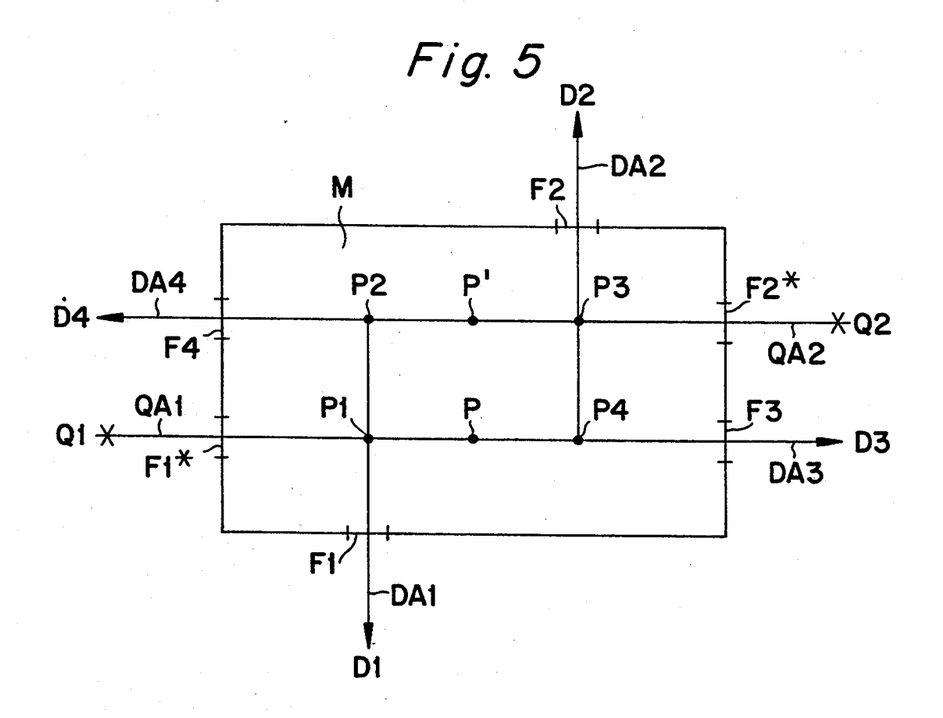
FIG. 5 a schematic representation of a combination in accordance with the invention of the multiple-beam processes for 90° scattered light measurement and 120° backscatter measurement having two sources and four detectors, seen from above.

FIG. 5 shows a schematic representation of a combination in accordance with the invention of the multiple-beam processes for a 90° scattered light measurement and a 120° backscatter measurement having two sources and four detectors, seen from above.

In this arrangement the multiple-beam process for a 90° scattered light measurement comprises sources Q1 and Q2 with corresponding source axes QA1 and QA2, particles P or P′, detectors D3 and D4 with corresponding detector axes DA3 and DA4, windows F1°, F2°, F3 and F4, and substance M to be measured.

The light from the source Q1 is carried to particle P of the substance M to be measured. The light from the source Q2 is carried to particle P′ of the substance M to be measured.

At least approximately, and more preferably exactly, the detector axis DA3 of the detector D3 coincides with source axis QA1. Detector D3 detects the transmitted light of formula (5.1), at least approximately, and in more preferably exactly, the detector axis DA4 of detector D4 coincides with source axis QA2. The detector D4 detects the transmitted light in accordance with formula (5.2):

$$I_1/I_{D31} = exp(c\epsilon d)/(A_{F1} \cdot A_{F3}) \tag{5.1}$$

$$I_2/I_{D42} = exp(c\epsilon d)/(A_{F2} \cdot A_{F4}) \tag{5.2}$$

The detector axis DA4 of detector D4 is perpendicular to the source axis QA1. Detector D4 detects the scattered light from the particle P in accordance with formula (5.3); the detector axis DA3 of detector D3 is perpendicular to source axis QA2. Detector D3 detects the scattered light from the particle P' in accordance with formula (5.4):

$$I_1/I_{D41} = exp(c\epsilon d)/(\alpha_{90} c A_{F1} \cdot A_{F4}) \quad (5.3)$$

$$I_2/I_{D32} = exp(c\epsilon d)/(\alpha_{90} c A_{F2} \cdot A_{F3}) \quad (5.4)$$

The vertical plane in which QA1 lies is disposed parallel to the vertical plane in which QA2 lies and nearly coincides with it. In particular, the vertical planes can coincide. The opening angle of D3 is such that it permits both a transmitted light measurement of Q1 and a scattered light measurement of the particle P'; the opening angle of D4 is such that it permits both a transmitted light measurement of Q2 and a scattered light measurement of the particle P.

In this arrangement, the multiple-beam process for a backscatter measurement comprises sources Q1 and Q2 with corresponding source axes QA1 and QA2; particles P1 or P2, P3 or P4, respectively; detectors D1 and D2 with corresponding detector axes DA1 and DA2; windows F1°, F2°, F1 and F2; and the substance M to be measured.

Detector axis DA1 of detector D1 is disposed such that detector D1 can detect the backscatter of the particle P1 in accordance with formula (5.5) and the backscatter of the particle P2 in accordance with formula (5.6) at an angle of 120°; detector axis DA2 of detector D2 is disposed such that the detector D2 can detect the backscatter of the particle P3 in accordance with formula (5.7) and the backscatter of the particle P4 in accordance with formula (5.8) at an angle of 120°:

$$I_1/I_{D11} = exp(c\epsilon d_1)/(\alpha_{120} A_{F1} \cdot A_{F1}) \quad (5.5)$$

$$I_1/I_{D12} = exp(c\epsilon d_2)/(\alpha_{120} A_{F2} \cdot A_{F1}) \quad (5.6)$$

$$I_2/I_{D22} = exp(c\epsilon d_1)/(\alpha_{120} c A_{F2} \cdot A_{F2}) \quad (5.7)$$

$$I_2/I_{D21} = exp(c\epsilon d_2)/(\alpha_{120} c A_{F1} \cdot A_{F2}) \quad (5.8)$$

By means of a corresponding arrangement, it is ensured that on the one hand the two light paths $d_1$, namely F1°-P1-F1, and $d_3$, namely F2°-P3-F2, in the substance M to be measured are identical in size and, on the other hand, that the two light paths $d_2$, namely F2°-P2-F1, and $d_4$, namely F1°-P4-F2, in the substance M to be measured are identical in size. In this case $d_1$ is the shorter light path, and $d_2$ is the longer light path.

Relationships (5.1) to (5.3) and (5.2) to (5.4) are formed in pairs from the 4 measured values in accordance with formulas (5.1) through (5.4), resulting in formulas (5.9) and (5.10):

$$I_{D41}/I_{D31} = \alpha_{90} c A_{F4}/A_{F3} \quad (5.9)$$

$$I_{D32}/I_{D42} = \alpha_{90} c A_{F3}/A_{F4} \quad (5.10)$$

Formulas (5.9) and (5.10) are likewise independent of source intensities $I_1$ and $I_2$ and of the damping $exp(c\epsilon d)$ in the substance to be measured.

If sources Q1 and Q2 are controlled such that condition (5.11) is met, then the result (5.12) is obtained through the multiplication of formula (5.9) with (5.10):

$$I_{D31} = I_{D42} = k \quad (5.11)$$

$$I_{D41} I_{D32} = (\alpha_{90} c)^2 k^2 \quad (5.12)$$

where the measured light intensities $I_{D41}$ and $I_{D32}$ are now dependent only on the scattering coefficient $\alpha_{90}$, a constant k and the solid concentration c.

Relationships (5.8) to (5.5) and (5.6) to (5.7) are formed in pairs from the 4 measured values in accordance with formulas (5.5) through (5.8), resulting in formulas (5.13) and (5.14):

$$I_{D11}/I_{D21} = exp[c\epsilon(d_2-d_1)] A_{F1}/A_{F2} \quad (5.13)$$

$$I_{D22}/I_{D12} = exp[c\epsilon(d_2-d_1)] A_{F2}/A_{F1} \quad (5.14)$$

Formulas (5.13) and (5.14) are independent of source intensities $I_1$ and $I_2$ and of the scattering coefficient $\alpha_{120}$ in the substance to be measured.

If sources Q1 and Q2 are-controlled such that condition (5.15) is met, then the result (5.16) is obtained through the multiplication of formula (5.13) with (5.14):

$$I_{D21} = I_{D12} = k \quad (5.15)$$

$$I_{D11} I_{D22} = k^2 exp[2c\epsilon(d_2-d_1)] \quad (5.16)$$

where the measured light intensities $I_{D11}$ and $I_{D22}$ are now dependent only on the difference between light paths $d_1$ and $d_2$, which are constant; on the absorption coefficient $\epsilon$; on a constant k; and on the solid concentration c. Formulas (5.1) through (5.16) apply with the omission of multiple scatterings.

By means of an electrical trigger circuit, light intensities $I_1$ and $I_2$ are generated in light emitting diodes, for example in GaAs light emitting diodes, GaAlAs light emitting diodes or laser diodes and absorbed into the substance M to be measured. Afterward light intensities $I_{D11}$, $I_{D12}$, $I_{D21}$, $I_{D22}$, $I_{D31}$, $I_{D32}$, $I_{D41}$ and $I_{D42}$ are measured, which are converted into electrical signals in silicon photodiodes, PIN diodes, avalanche diodes or photomultipliers. The signals are supplied to a signal processing means, by means of which the solid concentrations in the substance to be measured are ascertained.

Detectors D1-D4 each detect light from both sources Q1 and Q2. If the sources are operated with differently modulated light, the two portions can be separated in the detector signals in a known way. Types of modulation that come into consideration are the use of variation in light intensity having a pulse-duty factor of 50%, pulse operation having a pulse-duty factor much smaller than 50%, and other known types of modulation.

It is known that the conversion characteristic of the optoelectronic components is subject to aging and is very temperature-dependent. These dependencies, as well as the dependency on the soiling of windows F1°, F2°, F1, F2, F3 and F4, are compensated for by means of the multiple-beam principle.

The distance between the two vertical planes in which source axes QA1, QA2, which are perpendicular to one another, are located is dependent on light paths $d_1$ and $d_2$ and on the angle $\gamma$ of the backscatter measurement.

By means of the special arrangement of the two source axes QA1 and QA2 with respect to detector axes DA1/-DA4, it is possible to execute the 90° scattered light process and the backscatter process as multiple-beam processes with only two sources, which proves to be particularly advantageous.

Figure 6:
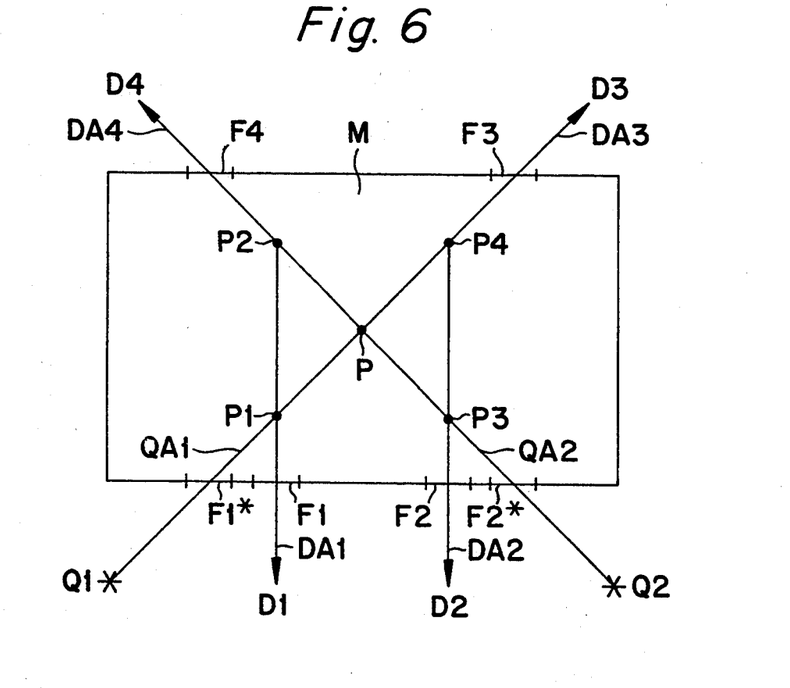
FIG. 6 a schematic representation of a combination in accordance with the invention of the multiple-beam processes for 90° scattered light measurement and 120° backscatter measurement having two sources and four detectors, seen from the side.

FIG. 6 shows a schematic representation of a combination in accordance with the invention of the multiple-beam processes for a 90° scattered light measurement and a backscatter measurement having two sources and four detectors, seen from the side.

In this figure, reference numerals Q1, Q2, QA1, QA2, D1-D4, DA1-DA4, M, P, P1, P2, P3, P4, F1°, F2°, F1-F4 correspond to those in FIG. 5. The mode of operation has already been described in detail in FIG. 5.

Figure 7:
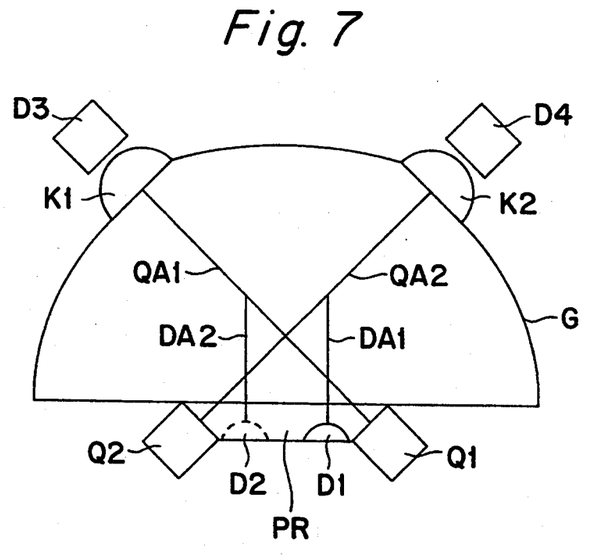
FIG. 7 a schematic representation of an exemplary embodiment having 2 sources and 4 detectors, seen from the side.

FIG. 7 shows a schematic representation of an exemplary embodiment having 2 sources and 4 detectors, seen from the side.

A prism PR, via which the light from sources Q1 and Q2 is coupled in, is mounted on the housing G. Two condenser lenses K1 and K2 are mounted on the housing G, and the transmitted light from sources Q1 and Q2 and the 90° scattered light is supplied to detectors D3 and D4, which are located behind the condenser lenses, after interaction with the substance M to be measured, which is located in the housing. Along with sources Q1 and Q2, two further detectors D1 and D2 that serve to measure backscatter are mounted at the prism.

The housing G can be made of black-anodized aluminum, for example; materials such as sapphire, quartz or conventional glass are possible for condenser lenses K1 and K2. The condenser lenses are glued in the housing.

Two model SFH 414 (Siemens) light emitting diodes, with which short light pulses are generated are used as sources Q1 and Q2. The repetition rate is 1 kHz, with a pulse-duty factor of 5%, a light wavelength of 950 nm and a projection angle of +/− 11°. By means of prism PR, which will be described in detail below, the beams are coupled into the substance to be measured in the housing at an angle of 45°. Source axes QA1 and QA2 are perpendicular to one another, and the vertical planes in which they lie are spaced apart by 2.8 mm. Source axes QA1 and QA2, from a distance of 40 mm, strike the respective opposed condenser lenses K1 and K2, which have a diameter of 19 mm. Detectors D3 and D4 are mounted near the focal point, behind the condenser lenses. The transmitted light from Q1 and the 90° scattered light are measured with D3, and the transmitted light from Q2 and the 90° scattered light from Q1 are measured with D4. SFH 2030 (Siemens) silicon photodiodes are used as detectors D3 and D4. The photocurrents of these diodes are processed in an electronic circuit, and the solid concentration c is calculated from the measuring results by means of formulas (5.11) and (5.12), taking into consideration the scatter coefficient $a_{90}$.

As the solid concentration c rises, the transmitted light becomes increasingly weaker and the accuracy of measurement drops. Above a limit dependent on the substance to be measured, the solid concentration is advantageously calculated from the backscattered light.

By means of the same prism PR that is used for coupling in light, the backscatter is coupled out at two locations located opposite one another, at a 45° angle; in the direction of detector axes DA1 and DA2. The directions of the two outcouplings are at a 120° angle to source axes QA1 and QA2. Detectors D1 and D2 are located below the outcoupling locations. The light paths in the substance to be measured from source Q1 to the detector D1 and from source Q2 to the detector D2 have an average length of 8 mm; the light paths in the substance to be measured from source Q2 to the detector D1 and from source Q1 to detector D2 have an average length of 16 mm. SFH 2030 silicon photodiodes are likewise used as detectors D1 and D2.

The photocurrents of these diodes are processed in an electronic circuit, and the solid concentration c is calculated from the measured results by means of formulas (5.15) and (5.16), taking into consideration the absorption coefficient $\epsilon$.

Figure 8:
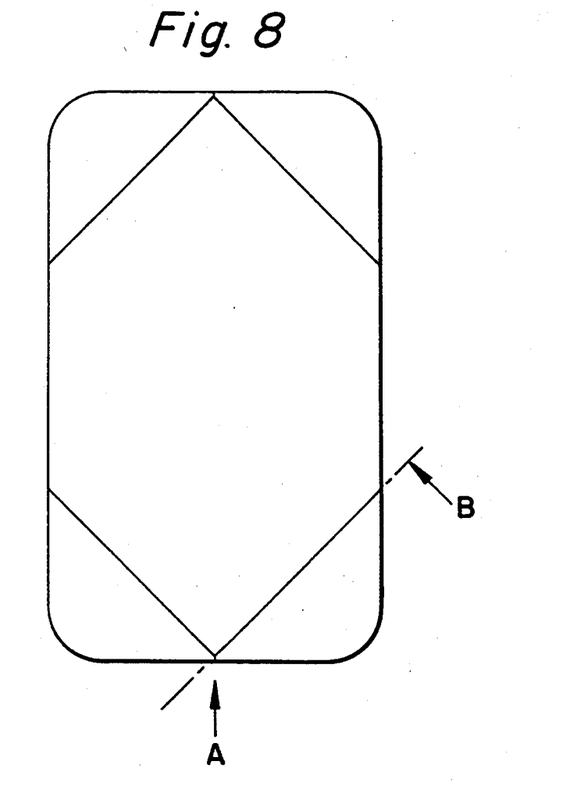
FIG. 8 the prism of FIG. 7 in a top view.

FIG. 8 shows the prism of FIG. 7 in a top view. The prism is advantageously made of sapphire that has a refraction index of 1.76, but can also be made of quartz that has a refraction index of 1.45, or conventional glass. The prism is glued inside the housing.

Figure 9A:
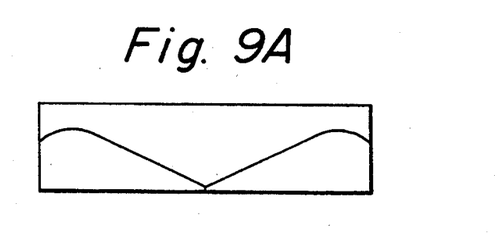
FIG. 9A the prism of FIG. 7 in view A.
Figure 9B:
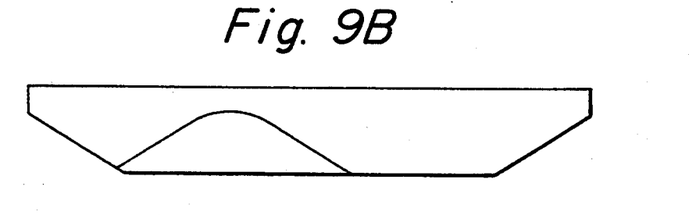
FIG. 9B the prism of FIG. 7 in view B.

FIG. 9A and FIG. 9B show the prism of FIG. 7 in view A and view B, respectively.

Figure 10:
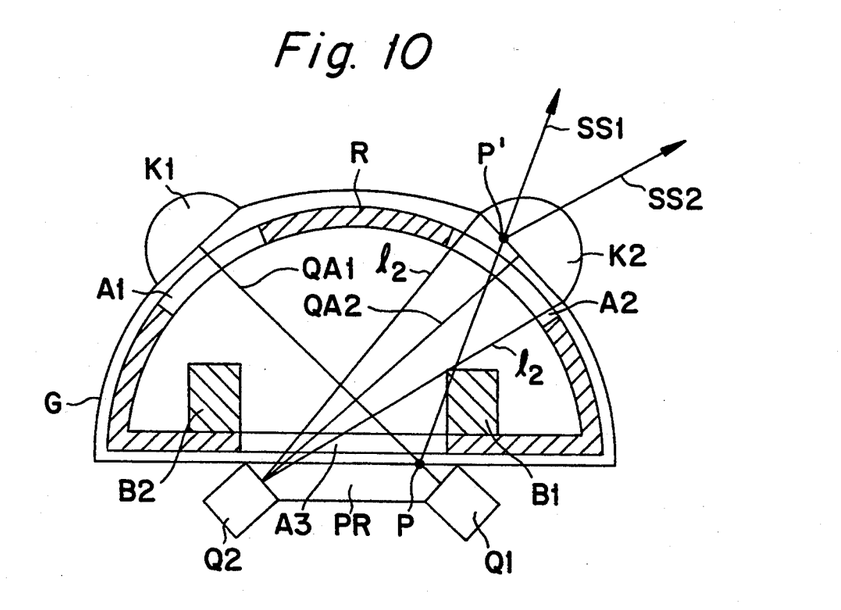
FIG. 10 a schematic representation of a second exemplary embodiment having a cleaning element and two screens, seen from the side.

FIG. 10 shows a second exemplary embodiment having a cleaning element and two screens, shown from the side.

No measuring errors result from soiling of the optical components, because these errors are compensated for by the multiple-beam process; however, the total quantity of light that can be evaluated decreases, and this lowers the resolution capability of the measuring array.

A cleaning element R, in which recesses A1, A2 and A3 are provided, is located in housing G, to which condenser lenses K1 and K2 and prism PR are secured. In the resting state, that is, when the cleaning element is inactive, these recesses are located precisely above the prism and condenser lenses. The cleaning element is displaceably disposed for a movement perpendicular to source axes QA1 and QA2. The element can be provided with a pneumatic drive, for example. The movement of the cleaning element is arranged such that it sweeps over at least the entire surface of the prism and condenser lenses. Afterwards the cleaning element is returned to its resting state. Depending on the type and concentration of the substance to be measured, the necessity arises at various time intervals to eliminate the soiling on the prism and condenser lenses by activating the cleaning element. The cleaning element can be made of black-colored plastic or hard rubber, for example. Screens B1 and B2, which are used to screen out parasitic scattered light, are disposed on cleaning element R. Source Q2, with its source axis QA2 and the boundaries $l_2$ of the light cone, is aimed at the condenser lens K2. Parasitic scattered light can arise under the following conditions, for example, and can be eliminated by means of screen B1: after passing through the prism, the light from source Q1, which with its source axis QA1 is aimed at the condenser lens K1, strikes a particle or scratch at location P on the prism surface, and because of this is scattered in different directions, but particularly in the direction of condenser lens K2, as is indicated by a scattered light beam SS1. If a particle or scratch is located at location P' on the condenser lens K2, then further scattering occurs, after which in particular a scattered light beam SS2 causes a quantity of parasitic scattered light on the detector located behind the condenser lens K2. The screen B1 is disposed such that it screens out the scattered light beams SS1 before they strike the condenser lens K2, but without affecting the light cone of source Q2. The screen B1 can be mounted on the cleaning element R, or be embodied as an integrated component of cleaning element R.

Figure 11:
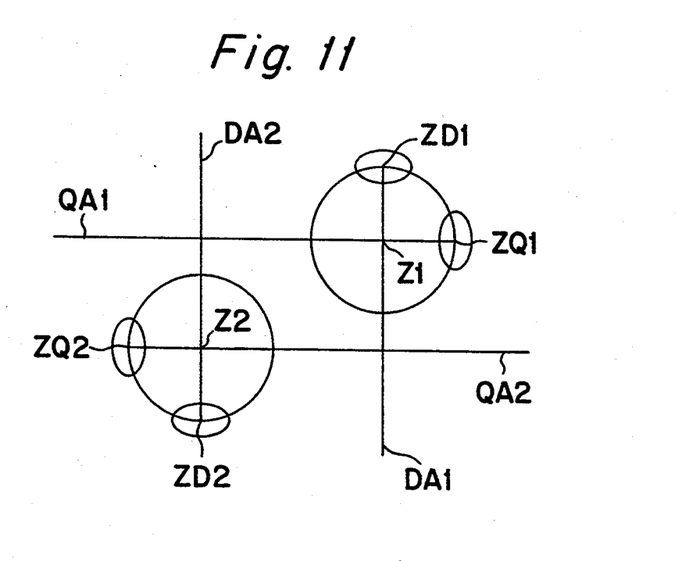
FIG. 11 a schematic representation of a third exemplary embodiment for the arrangement of two sources and two detectors, seen from above.

FIG. 11 shows a schematic representation of a third exemplary embodiment for the arrangement of two sources and two detectors in the housing, seen from above.

A conical bore whose opening angle is 90 degrees, for example, is disposed perpendicular to the housing surface and has a center Z1 and Z2. Bores having centers ZQ1, ZQ2, ZD1 and ZD2 and at an angle of 90 degrees, for example, from the cone surface, are provided for source axes QA1 and QA2 and detectors DA1 and DA2. This creates four recesses, in which the windows, for example made of sapphire, are glued, behind which sources Q1 and Q2 and detectors D1 and D2 are located. This arrangement meets the conditions for backscatter measurement.

With such measuring devices according to the invention as shown in FIGS. 5–11, a broader measuring range for fresh water can be detected, ranging from the slightest contamination, for example a dissolution of 0.1 NTU, to sludge, for example with solid concentrations up to 200 g/l, and continuous measurement over the entire range is possible.

If only high solid concentrations are measured, then the arrangement of detectors D3 and D4, and condenser lenses K1 and K2, can be omitted; that is, the 90° scattered light measurement can be omitted.

Applications for a device of this type and associated processes are the measurement of solid concentrations in water technology, waste water technology, particularly in sewage processing systems, where very high sludge concentrations must be dealt with; foodstuff technology, for example the production of fruit concentrates, the pharmaceutical industry; and in the area of biotechnology, particularly to determine biomass, in the determination of growth rates in cell cultures.

It is essential to the invention that solid concentrations, particularly low as well as high, can be detected in a single measuring array with a multiple-beam process using a combined measuring process that comprises, on the one hand, a 90° scattered-light process and, on the other hand, a backscatter process; only two sources are used, and the corresponding signals are evaluated with the same electronics. The multiple-beam process, which is based on 2 measurements through exactly the same window surface, permits effective compensation for undesired soiling of the window surfaces and aging of the optoelectronic components.

The foregoing has described the preferred principles, embodiments and modes of operation of the present invention; however, the invention should not be construed as limited to the particular embodiments discussed. Instead, the above-described embodiments should be regarded as illustrative rather than restrictive, and it should be appreciated that variations, changes and equivalents may be made by others without departing from the scope of the present invention as defined by the following claims.

What is claimed is:

1. A device for measuring solid concentrations in liquids, comprising:
   a housing for containing a substance to be measured, having windows to allow the passage of light into and out of the housing;
   two light sources mounted on the housing, each light source generating a light cone having a source axis that projects into the housing; and
   at least two light detectors mounted on the housing, each detector having a detector axis that projects into the housing;
   wherein the source axes of the light cones are at least substantially perpendicular to one another and lie in at least substantially parallel planes;
   wherein a first detector axis is disposed to intersect a first source axis at a first point with a first light path $d_1$ in the substance to be measured, and to intersect a second source axis at a second point with a second light path $d_2$ in the substance to be measured, the second light path $d_2$ being longer than the first light path $d_1$; and
   wherein a second detector axis is disposed to intersect the second source axis at a third point with a light path $d_3$ in the substance to be measured and to intersect the first source axis at a fourth point with a light path $d_4$ in the substance to be measured, the fourth light path $d_4$ being longer than the third light path $d_3$.

2. A device in accordance with claim 1, further comprising a third detector mounted on the housing and having a third detector axis substantially in alignment with the first source axis, and a fourth detector mounted on the housing and having a fourth detector axis substantially in alignment with the second source axis.

3. A device in accordance with claim 2, wherein a ratio of the length of the light path, in the substance to be measured, from the first source to the third detector to the length of the light path, in the substance to be measured, from the first source to the first detector, and the ratio of the length of the light path, in the substance to be measured, from the second source to the fourth detector to the length of the light path, in the substance to be measured, from the second source (Q2) to the detector, is in a range between 1 and 10.

4. A device in accordance with claim 3, wherein the ratio is 5.

5. A device in accordance with claim 1, wherein the first and second source axes and the first and second detector axes are disposed to project into the housing through windows disposed in conically shaped portions of the housing.

6. A device in accordance with claim 1, further comprising a prism mounted on the housing and disposed so that the source axes and detector axes are covered upon entrance into the housing, the prism being flat on at least on one side.

7. A device in accordance with claim 1, wherein the light sources comprise light emitting diodes, selected from the group consisting of GaAs diodes, GaAlAs diodes and laser diodes.

8. A device in accordance with claim 7, wherein the detectors comprise a device selected from the group consisting of silicon PIN diodes, avalanche diodes and photomultipliers.

9. A device in accordance with claim 1, wherein a ratio of the length of the light path, in the substance to be measured, from the first source to the first detector to the length of the light path, in the substance to be measured, from the first source to the second detector, and a ratio of the length of the light path, in the substance to be measured, from the second source to the second detector to the length of the light path, in the substance to be measured, from the second source to the first detector, is in a range of less than 1.

10. A device in accordance with claim 9, wherein the ratio is 0.5.

11. A device in accordance with claim 1, further comprising a device for cleaning the windows comprising a displaceably seated, piston-shaped cleaning element.

12. A device in accordance with claim 1, further comprising means disposed on the cleaning element to screen out parasitic scattered light.

13. A device in accordance with claim 1, wherein the source axes of the light cones generated by the light sources lie in the same plane.

14. A process in accordance with claim 1, further comprising the step of providing a substance to be measured, wherein the solid concentration measured determines the biomass of the substance.

15. A process for measuring solid concentrations in liquids in a device having a housing for a substance to be measured, a first and second light source each for generating light on an axis into the housing, and a first and second detector for detecting light exiting the housing, wherein a first detector axis is disposed to intersect a first source axis at a first point with a first light path $d_1$ in the substance to be measured, and to intersect a second source axis at a second point with a second light path $d_2$ in the substance to be measured, the Second light path $d_2$ being longer than the first light path $d_1$, and wherein a second detector axis is disposed to intersect the second source axis at a third point with a light path $d_3$ in the substance to be measured and to intersect the first source axis at a fourth point with a light path $d_4$ in the substance to be measured, the fourth light path $d_4$ being longer than the third light path $d_3$, comprising the steps of:

modulating differently the light sources;

measuring the backscatter intensities $I_{D11}$ and $I_{D21}$ in light path $d_1$ and backscatter intensifies $I_{D12}$ and $I_{D21}$ in light path $d_2$;

determining ratios $I_{D11}/I_{D21}$ and $I_{D22}/I_{D12}$;

controlling the light sources so that $I_{D21}$ equals $I_{D12}$ equals k;

converting the backscatter intensities $I_{D11}$ and $I_{D22}$ into electrical signals; and detecting the solid concentration c in accordance with the mathematical relation $$I_{D11} I_{D22} = k^2 exp(2c\epsilon(d_2 - d_1))$$

wherein the variable $I_{Dji}$ indicates the light intensity of source i at detector j; k indicates a constant; and $\epsilon$ indicates the absorption coefficient.

16. A process in accordance with claim 15 wherein the apparatus includes a third detector having a third detector axis aligned with the first source axis and perpendicular to the second source axis and a fourth detector having a fourth detector axis aligned with the second source axis and perpendicular to the first source axis, the method further comprising the steps of:

measuring the transmitted light intensities $I_{D31}$ of a light path from the first source to the third detector and $I_{D42}$ of a light path from the second source to the fourth detector and the 90° scattered light intensities $I_{D41}$ of a light path from the first source to the fourth detector and $I_{D32}$ of a light path from the second source to the third detector;

calculating the ratios $I_{D41}/I_{D31}$ and $I_{D32}/I_{D42}$;

controlling the sources so that $I_{D31}$ equals $I_{D42}$ equals k;

converting the 90° scattered light intensities $I_{D41}$ and $I_{D32}$ into electrical signals; and determining the solid concentration c for low solid concentrations in accordance with the mathematical relation $$I_{D41} I_{D32} = (\alpha_{90} c)^2 k^2;$$

and for high solid concentrations in accordance with the mathematical relation $$I_{D11} I_{D22} = k^2 exp(2c\epsilon(d_2 - d_1))$$

and wherein $\alpha_{90}$ indicates the scatter coefficient of the 90° scattered light measurement.

17. A process in accordance with claim 15 for measuring solid concentrations in water technology further comprising the step of providing a substance to be measured from the group consisting of waste water treatment products, sewage processing systems products; foodstuff processing products; pharmaceutical processing products; and biotechnology processing.

* * * * *